United States Patent [19]

Flett et al.

[11] Patent Number: 4,921,221

[45] Date of Patent: May 1, 1990

[54] MONITORING PYROGENIC PROCESSES

[75] Inventors: Douglas S. Flett; Gary Holt; Peter J. Tily, all of Stevenage, Great Britain

[73] Assignee: Secretary of State for Trade and Industry, Minerals and Metals Division, Warren Springs Laboratory, Stevenage-Hertfordshire, United Kingdom

[21] Appl. No.: 265,708

[22] Filed: Nov. 1, 1988

[30] Foreign Application Priority Data

Nov. 3, 1987 [GB] United Kingdom ............... 8725741

[51] Int. Cl.$^5$ .............................................. C22B 1/00
[52] U.S. Cl. .................................... 75/385; 266/80
[58] Field of Search ............... 266/78, 80, 99; 75/25, 75/78, 77, 68 R

[56] References Cited

U.S. PATENT DOCUMENTS 4,004,921 1/1977 Beaton et al. ...................... 75/77
4,250,027 2/1981 Cases et al. ........................ 75/25

Primary Examiner—S. Kastler
Attorney, Agent, or Firm—Fleit, Jacobson, Cohn, Price, Holman & Stern

[57] ABSTRACT

Pyrogenic processes in which gas or fume is evolved are monitored by impinging a beam of X-rays (3) from an X-ray source (1) on the gas or fume whereby radiation is produced by the X-ray fluorescence which is detected by a radiation detector (7) and analyzed by an analyzer (8) for the various constituent elements. In this way the progress of the metallurgical process can be monitored and the information used for process control.

20 Claims, 1 Drawing Sheet

MONITORING PYROGENIC PROCESSES

BACKGROUND OF THE INVENTION

This invention relates to monitoring pyrogenic processes, and in particular to a method and to apparatus for monitoring pyrogenic processes such as combustion or pyrometallurgical processes, the latter being processes wherein metal compounds are processed at relatively high temperatures, so as to recover metal values from the raw materials, while producing process off-gases, and includes distillation of metals and metal compounds.

Although process modelling is established for a limited number of pyrometallurgical processes, e.g. the blast furnace for iron making, such models rely heavily on constant feed rates and composition, idealization of conditions and a knowledge of fundamental kinetic data. Without the latter, models are worthless in their ability to predict the state of reaction.

If no process model exists, reliance must be placed on either the experience of the process operators or the monitoring or sampling of the process or process streams. Accurate sampling of the phases in the furnace itself is often difficult and sometimes impossible. However, where a pyrometallurgical process generates gases, vapor, fume or dust, the composition thereof and the way in which this changes over time can be used as an indication of the extent or state of reaction within the furnace. Manual sampling of the fume and subsequent chemical analysis is sufficiently time consuming and labor intensive as to be an impractical on-stream method for process monitoring.

BRIEF DESCRIPTION OF THE INVENTION

In a first aspect, the present invention provides a method of monitoring a pyrogenic process, in particular monitoring gases in or from a pyrogenic process, comprising directing a beam of X-rays into a furnace, combustion chamber, flue or duct carrying a gas-stream leaving a pyrogenic reactor, detecting the radiation produced by fluorescence of elements present in the gas-stream by means of an X-ray detector, and passing the output of the detector to an analyzer which allows the radiation intensities corresponding to individual elements to be measured.

In a second aspect, the invention provides apparatus for a pyrogenic process, in particular monitoring gases in or from a pyrogenic process, comprising a primary X-ray source in a housing adapted to be installed on a furnace, combustion chamber, flue or duct carrying off-gases from a pyrogenic reactor, an X-ray detector off-set from the source, adapted to receive radiation produced by fluorescence of elements contained in the off-gas, and an analyzer adapted to receive and analyze the radiation received from the detector into the contributions made by individual elements.

The preferred pyrogenic process is a pyrometallurgical one. The pyrometallurgical process is suitably the fuming of volatile metals or their compounds from slags or other molten metallurgical phases.

Alternatively, the process may be suitably a primary or secondary smelting or refining process, or may be a roasting or other solid state oxidation or reduction process.

The pyrogenic process may alternatively be a combustion process.

The apparatus preferably comprises a primary X-ray source set into a specially designed mounting which produces a beam of X-rays that are directed into the furnace itself or a flue or duct carrying the off-gases from a kiln, furnace or other type of reactor used in pyrometallurgical processing. An X-ray detector offset from the X-ray source in the same mounting detects any fluorescence produced by excitation of the elements present in the gases, vapor, fume or dust. By careful arrangement of the angle of inclination of the X-ray tube and the detector, and by providing collimation on both the X-ray tube and the detector, it is possible to ensure that the detector does not pick up any excitation from either deposited fume or condensate on the walls of the duct or the materials constituting the walls. The detector only senses the fluorescent excitation produced by the gases, vapor, fume and dust components in the off-gases leaving the high temperature reactor.

As the relative sensitivity of the detector to a given element is a function of that element's characteristic energy, it is necessary to ensure that the X-ray source has sufficient energy to produce the desired degree of excitation. A voltage source of 50 kV would be capable of producing a detectable response from elements in the atomic table, typically from sulphur upwards.

The output from the detector is amplified and the signal may be fed to a remote multi-channel analyzer from which the required X-ray intensities can be computed and displayed. The multi-channel analyzer suitably comprises a large number of channels each covering a small voltage range. An incoming X-ray energy related voltage pulse from the detector is input as a count into the appropriate channel relative to that voltage level. The process is repeated for all incoming pulses to build up a spectrum of counts in each of the levels. By calibration with known X-ray sources, the resulting spectrum can be calibrated into energies and thus the peaks present in the spectrum can be identified. Typically it might be necessary to record the detector output for a period of 50–100 seconds to obtain sufficient counts to build up a spectrum. Consequently, although the detector is operating on-line, only one spectrum and therefore only one measurement of concentration is obtained every counting period.

Alternatively it is possible to set up one or more single channel analyzers to which the detector signals are fed.

The single channel analyzer is essentially an adjustable voltage window detector which will only pass voltage pulses between defined levels. The levels are adjusted to specific particular X-ray peaks. The output from the single channel analyzer thus relates to a specified element and this can be passed to a rate meter to provide an analog indication in counts per second for any element of interest. It is then a continuous analytical system for any particular element or elements present in the gases, vapor, fume or dust.

The process is applicable to batch or continuous pyrometallurgical processes.

Examples of batch processes to which the invention is applicable include fuming of tin and zinc from slags and other metal-bearing materials, cupellation processes and refining of primary and secondary materials e.g. copper, lead, tin.

Examples of continuous processes to which the invention is applicable include shaft-furnace smelting, fluidized-bed roasting and high intensity smelting processes, e.g. plasma arc furnaces.

Advantages of the use of apparatus according to the invention are as follows:

The apparatus can monitor the composition of the gases, vapor, fume or dust for all elements typically from sulphur upwards in the atomic table, qualitatively and quantitatively.

The apparatus can be used to determine reaction end-points in batch processing by measuring the changing composition of a component or components present in the gases, vapor, fume or dust. Thus it can be used to prevent excessive processing times and unnecessary losses of metal values.

The apparatus can also be used at elevated temperatures where existing physical sampling methods are impractical. This is seen as a major advantage of the system over other methods as it allows the gases, vapor, fume or dust to be analyzed before it is affected by down-stream processing e.g. quenching, dilution, physical dropout, mixing.

The apparatus can also detect low levels of a component present in a gas, vapor, fume or dust containing a high concentration of other elements. It can thus detect and record a number of elements over a wide range of concentrations. This can be important when checking for losses of valuable metal components.

The apparatus is sensitive enough for it to be used for monitoring stack emissions for environmental purposes. For example, gases from the combustion of fossil fuels may be monitored.

The apparatus is not restricted to use in batch processing. Where the process is of a continuous nature, the analyzer can detect departures from steady-state conditions which produce changes in the gas, vapor, fume or dust composition, e.g. in fluid bed roasting of sulphidic ores it can be used to monitor the total sulphur as sulphide, sulphate and sulphur dioxide in the off-gases, in fuming processes it can be used to control selectively fuming rates, and in the combustion of fossil fuels it can be used to monitor the sulphur dioxide content in the off gases.

BRIEF DESCRIPTION OF THE DRAWINGS

The invention will be further described with reference to the following illustrative examples which relate to various pyrometallurgical processes using apparatus of the invention according to the single invention wherein: A suitable apparatus is illustrated in the accompanying drawing.

DETAILED DESCRIPTION

Figure 1:
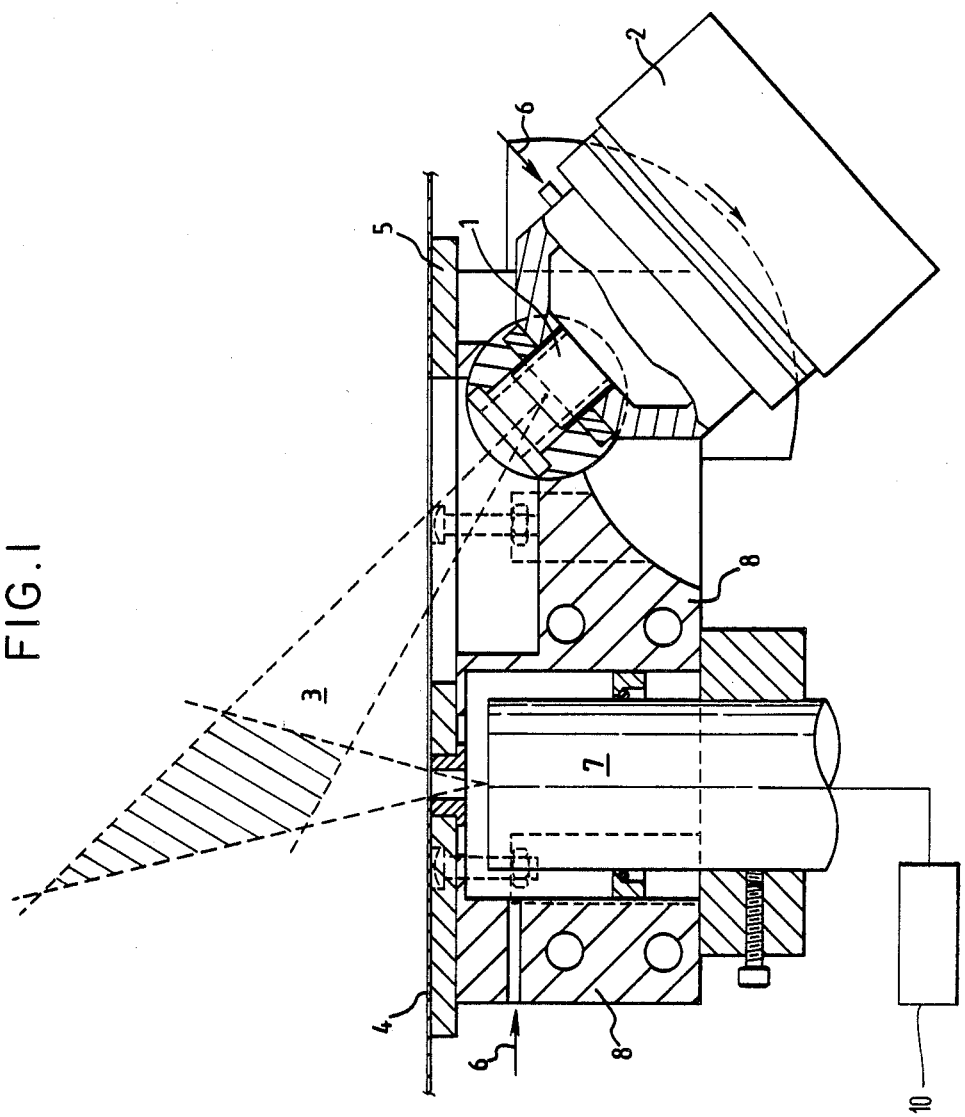
FIG. 1 is a partly cross sectional side view of the apparatus of the invention.

The apparatus shown in the drawing comprises a source of X-rays, generally designated 1, mounted in a swivel mounting block 2 which is fixed externally to a furnace, duct, or flue and is adjustable so as to direct a beam of X-rays 3 into a furnace, duct, or flue bounded by a wall 4 at a pre-determined angle. A water-cooled housing 5 and an air purge, or flushing system 6 serve to protect the X-ray source from the heat, fume and dust of the gases carried by the duct. An X-ray detector 7 is mounted in a main block 8 in a position off-set from X-ray source 1 so as to receive radiation produced by fluorescence of the elements irradiated by the X-rays passing into the duct from the source 1. The output from the detector 7 is passed to a multi-channel analyzer, rate meter, or other counting device 10.

EXAMPLE 1—FUMING OF TIN FROM SLAG 100 kg of a tin slag containing approximately 6% Sn was charged to a pilot-scale top blown rotary furnace and melted down. Iron pyrites was added to fume the tin as sulphide. The tin sulphide fume was oxidized at the mouth of the furnace, by dilution air, and the resultant tin oxide collected in a bag filter plant.

The X-ray fume (XRF) apparatus as shown in the drawing was mounted on the duct work between the furnace mouth and the bag filter plant. The response of the XRF system to the presence of the tin in fume was monitored throughout the fuming cycle, and samples of the tin slag were taken from the furnace at regular intervals as well a iso-kinetic fume samples. The samples of tin slag were analyzed and the XRF response to tin in the fume was correlated with the residual tin level in the slag and tin in the fume samples. From this, the fuming rate at the commercial reaction end-point of 0.3% Sn was, for this furnace arrangement, determined to be equivalent to 15 counts per second of tin on the read-out from the XRF apparatus.

On three subsequent tin fuming cycles, the process was terminated when the XRF response fell to this predetermined level of 15 counts per second. The assays of final slags were found to be 0.20%, 0.19% and 0.20% Sn respectively. Thus the XRF apparatus had accurately predicted on-line the commercial reaction end-point.

EXAMPLE 2—REFINING OF BLACK COPPER

Copper bearing scrap is recycled by smelting to produce a copper-based alloy containing iron, zinc, nickel, tin and lead. This impure copper, known as black copper, is refined in converters using air or oxygen-enriched air in two stages. In the first, iron and zinc are removed as a slag phase. Zinc fuming also occurs. In the second blow any residual zinc plus tin and lead are removed as a second slag or by fuming.

The XRF apparatus was mounted on the ductwork between a copper converter and its associated bag filter gas cleaning plant. The XRF system was then used over a period of weeks to determine the variation in the fuming levels of zinc, tin and lead. The variations seen indicated that it was possible to use the XRF response to control the process and effect a separation of the zinc and tin fume produced. As a result, tin losses to the first slag can be reduced and the tin content of the second fume increased.

EXAMPLE 3—FUMING OF ZINC FROM SLAGS

Zinc-bearing slags from the smelting of primary copper and lead concentrates are fumed at temperatures of 1100°–1300° C. Reductant is required to produce zinc-bearing vapor and this is usually blown into the molten slag with air through tuyeres. Secondary air is admitted above the bath to oxidized the zinc-bearing vapor which is subsequently collected as an oxide fume. During blowing, other elements also volatilize.

The XRF apparatus was mounted on the wall of a zinc fumer above the point where secondary air was admitted. The temperature of the gas phase being monitored was in excess of 1200° C. At this temperature the equipment was capable of showing continuously on-line variations in fuming rates of zinc, lead and arsenic.

The performance of the XRF apparatus long term was unaffected by the very high levels of radiation from the gas phase.

EXAMPLE 4—MONITORING OF SULPHUR IN PROCESS GAS STREAMS

During the converting of metal mattes, sulphur dioxide is produced by blowing with air or oxygen-enriched air. A knowledge of the sulphur dioxide content of the converter offgas or measure of the total sulphur removed can be used by furnace operators to determine when to terminate the blowing period. Conventional techniques for monitoring the sulphur dioxide content of gases, such as infra-red analysis, all involve sampling of the hot, often dirty, gases containing condensibles. These sample streams must then be thoroughly cooled and cleaned to avoid damage to the analytical equipment.

The XRF apparatus was mounted on the wall of a perspex vessel which could be filled with gas mixtures containing various levels of sulphur dioxide. The XRF apparatus was found to be capable of detecting sulphur dioxide at concentrations of 100 ppm by volume under these ideal conditions.

The XRF apparatus was then transferred to a duct containing a hot, dirty gas stream which was known to contain sulphur as sulphur dioxide, metallic sulphides and sulphates. The temperature of the duct was 500°-600° C. with fume loadings in excess of 100 g m$^{-3}$ at total sulphur levels of up to 5%. At these temperatures the fume was sticky, due to incipient melting, and thus conventional sampling was not possible. In this environment a positive response to the presence of sulphur was recorded which could be distinguished readily from other elements present in high concentrations.

In a similar way, the sulphur content of gases from the combustion of fossil fuels can be monitored.

We claim:

1. Apparatus for monitoring a pyrogenic process utilizing a furnace, combustion chamber, flue, and/or duct containing offgas produced by a pyrogenic reaction, comprising:
   a housing adapted for mounting on at least one of the furnace, combustion chamber, flue, and duct;
   a primary X-ray source mounted on said housing for producing a beam of X-rays directed into the offgas;
   X-ray detector means mounted on said housing in a position offset from said X-ray source for receiving radiation produced by X-ray fluorescence caused by said X-rays of elements in the offgas;
   said X-ray source and detector means being directed at an angle with respect to each other; and
   cooling and flushing means for passing cooling and flushing fluids through said housing for protecting said X-ray source and detector means from the environmental conditions of the off-gas.

2. The apparatus as claimed in claim 1 wherein:
   said housing has a mounting surface;
   said detector means has a central axis directed substantially perpendicular to said mounting surface; and
   said X-ray source has a central axis directed at a predetermined angle with respect to said axis of said detector means so that said X-ray beam from said source intersects said axis of said detector means within the off-gas being monitored.

3. The apparatus as claimed in claim 1 wherein:
   said X-ray beam and said detector means are collimated.

4. The apparatus as claimed in claim 2 wherein:
   said X-ray beam and said detector means are collimated.

5. The apparatus as claimed in claim 1 wherein:
   said cooling means comprises cooling passages in said housing for conducting cooling water therethrough.

6. The apparatus as claimed in claim 4 wherein:
   said cooling means comprises cooling passages in said housing for conducting cooling water therethrough. .

7. The apparatus as claimed in claim 1 wherein:
   said flushing means comprises channels in said housing and said X-ray source for conducting purging gas therethrough.

8. The apparatus as claimed in claim 4 wherein:
   said flushing means comprises channels in said housing and said X-ray source for conducting purging gas therethrough.

9. The apparatus as claimed in claim 6 wherein:
   said flushing means comprises channels in said housing and said X-ray source for conducting purging gas therethrough.

10. The apparatus as claimed in claim 1 wherein:
    adjustable means are provided for mounting said X-ray source on said housing for adjustment of the angle of said X-ray beam.

11. The apparatus as claimed in claim 9 wherein:L
    adjustable means are provided for mounting said X-ray source on said housing for adjustment of the angle of said X-ray beam.

12. The apparatus as claimed in claim 1 and further comprising:
    analyzer means operatively connected to said detector means for receiving and substantially instantly analyzing said radiation received by said detector means for indicating individual constituent elements of the off-gas.

13. The apparatus as claimed in claim 6 and further comprising:
    multi-channel analyzer means operatively connected to said detector means for receiving and substantially instantly analyzing said radiation received by said detector means for indicating individual constituent elements of the off-gas.

14. The apparatus as claimed in claim 11 and further comprising:
    multi-channel analyzer means operatively connected to said detector means for receiving and substantially instantly analyzing said radiation received by said detector means for indicating individual constituent elements of the off-gas.

15. A method of monitoring a pyrogenic process utilizing a furnace, combustion chamber, flue, and/or duct containing off-gas produced by a pyrogenic reaction comprising:
    directing a beam of X-rays from a primary X-ray source into the off-gas;
    producing X-ray fluorescence radiation by said beam from individual constituent elements in the off-gas;
    detecting and fluorescence radiation with a radiation detector; and
    analyzing said detected radiation into individual constituent elements of the off-gas.

16. A method as claimed in claim 15 and further comprising:

cooling the X-ray source and the detector to protect them against high temperature environment of the off-gas.

17. A method as claimed in claim 15 and further comprising:
flushing the area surrounding the X-ray source and the detector by gas purging to protect them against the environment of the off-gas.

18. A method as claimed in claim 16 and further comprising:
flushing the area surrounding the X-ray source and the detector by gas purging to protect them against the environment of the off-gas.

19. A method as claimed in claim 15 and further comprising:
directing said X-ray beam at a predetermined angle with respect to the direction of fluorescence radiation detected by the detector; and collimating said X-ray beam and said detector.

20. A method as claimed in claim 18 and further comprising:
directing said X-ray beam at a predetermined angle with respect to the direction of fluorescence radiation detected by the detector; and
collimating said X-ray beam and said detector.

* * * * *